United States Patent [19]

Harada

[11] Patent Number: 4,801,203

[45] Date of Patent: Jan. 31, 1989

[54] DETECTOR OF IMPURITIES IN MOLTEN SOLDER

[75] Inventor: Shigeo Harada, Ibaragi, Japan

[73] Assignee: Sharp Kabushiki Kaisha, Osaka, Japan

[21] Appl. No.: 106,953

[22] Filed: Oct. 6, 1987

Related U.S. Application Data

[63] Continuation of Ser. No. 734,567, May 15, 1985, abandoned.

[30] Foreign Application Priority Data

May 18, 1984 [JP] Japan ............................. 59-101520
Jul. 31, 1984 [JP] Japan ............................. 59-163223

[51] Int. Cl.$^4$ .................. G01N 21/88; B23K 1/00
[52] U.S. Cl. .................................. 356/237; 228/104
[58] Field of Search ............... 356/402, 445, 446, 237; 250/227; 436/2, 164; 228/104

[56] References Cited

U.S. PATENT DOCUMENTS

| | | | |
|---|---|---|---|
| 3,998,591 | 12/1976 | Eckfeldt | 356/445 |
| 4,040,749 | 8/1977 | David et al. | 250/227 |
| 4,342,919 | 8/1982 | Brogardh | 250/227 |
| 4,409,333 | 10/1983 | Tosima et al. | 436/2 |
| 4,491,412 | 1/1985 | Haroda et al. | 356/237 |
| 4,492,860 | 1/1985 | Brogardh et al. | 250/227 |

Primary Examiner—F. L. Evans
Attorney, Agent, or Firm—Flehr, Hohbach, Test, Albritton & Herbert

[57] ABSTRACT

A detector is adapted to detect the kinds and concentrations of impurity metals in molten solder or changes in the tin-lead composition of the solder by measuring the dissolution rate of a metallic film. The detector comprises a light-transmissive rod, the bottom cross-sectional area of which is covered by a metallic film. The top cross-sectional area of the rod is connected to an optical measurement means through an optical fiber cable and the time required to dissolve the metallic film in the sample molten solder is measured.

4 Claims, 3 Drawing Sheets

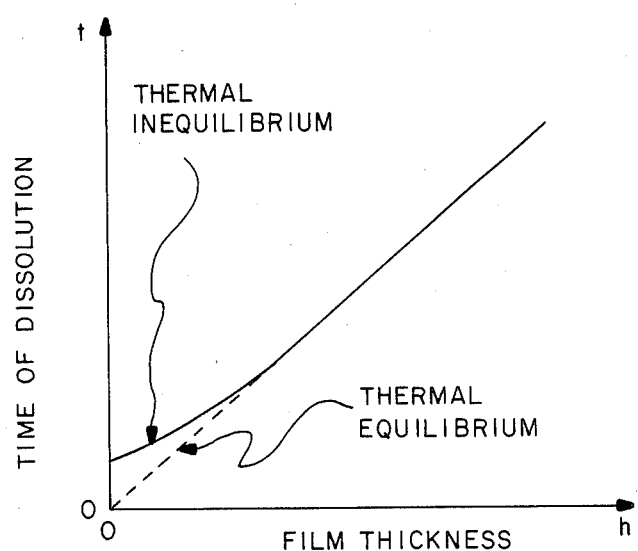
FIG. — 1
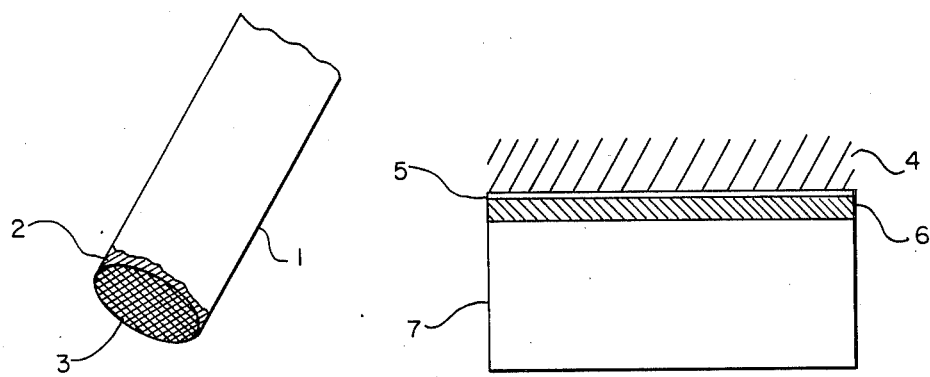
FIG. — 2         FIG. — 3

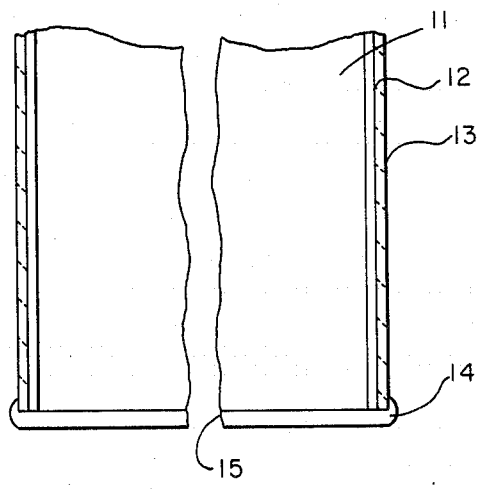
FIG.—4
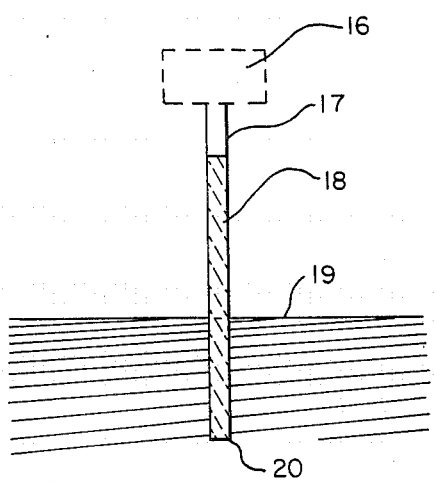
FIG.—5
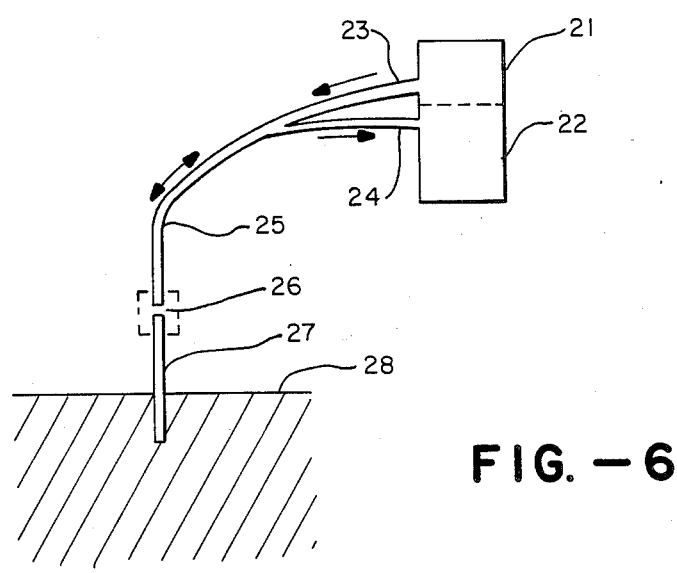
FIG.—6

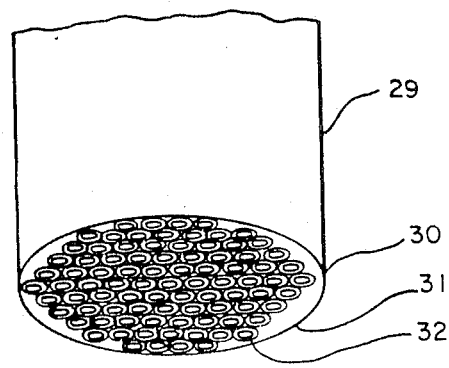
FIG.—7
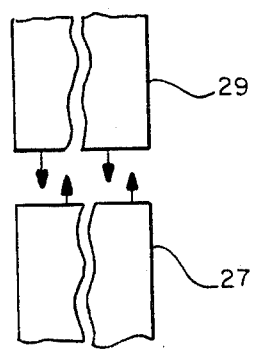
FIG.—8
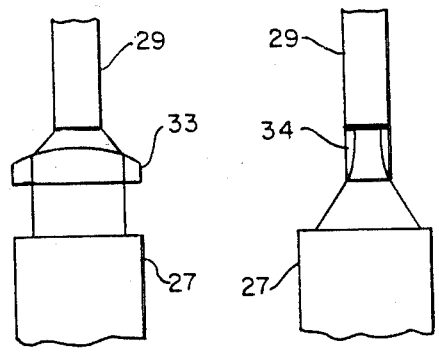
FIG.—9a   FIG.—9b
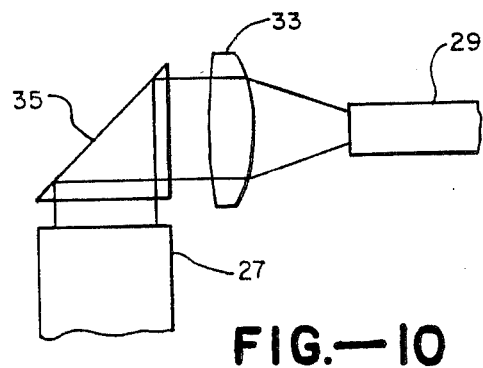
FIG.—10

DETECTOR OF IMPURITIES IN MOLTEN SOLDER

This is a continuation of application Ser. No. 734,567, filed May 15, 1985, now abandoned.

This invention relates to a device for detecting metal impurities in molten solder and changes in the solder composition.

With the development of automatic soldering systems, high-level management and control of molten solder have become important problems and many methods have been developed. In the past, methods by chemical analyses were mainly relied upon for the detection of metal impurities in molten solder and effects of their concentrations on solderability have been studied. When the copper concentration in molten solder exceeds 0.5 wt%, for example, the yield becomes significantly affected and either additional solder or tin must be added or the use of the solder must be terminated. Methods by chemical analyses are advantageous from the point of view of accuracy but analyses are time-consuming. Where speediness is of importance such as in a production line, therefore, they are not particularly to be favored.

For the testing of solderability, on the other hand, various tests on wetting characteristics have been utilized and methods based on physical phenomena such as meniscus testing have been considered for quantifying solderability and wetting characteristics. But the apparatuses for wetting tests are generally more complicated and expensive while results are not correspondingly accurate or reliable. Since these tests are difficult to conduct when the molten solder is actually being used, furthermore, there is an additional problem relating to speediness. A still further disadvantage of these methods is that no information can be obtained on the type of impurity metals, their concentrations or the consumption rate of tin in the molten solder.

With the recent advances in the electronics industries, more reliable solder control methods are needed. It has been pointed out that the conventional molten solder management and control methods are not sufficiently satisfactory in view of the rapid progress in various peripheral fabrication technologies.

More recently, a new improved method was proposed whereby the disadvantages described above can be eliminated. This method was based on the following two experimental results. Firstly, the concentration of an impurity metal in molten solder is closely related to the rate of dissolution of the same metal within a certain range and, secondly, the tin-lead composition in molten solder is closely related to the rate of dissolution of copper. On the basis of these experimental observations, this method comprises the steps of dissolving on the surface of molten solder a metallic film containing the same metal as the one to be detected in the solder and to estimate the concentration of this metal or the tin-lead composition in the solder form the measured rate of dissolution.

More in detail, a metallic film of thickness between 1 $\mu$m and 10 $\mu$m is formed by a vapor deposition or electroplating method on one surface of a borosilicate glass substrate of thickness between 0.20 mm and 0.30 mm. The film may be of a single layer structure or comprise a number of layers with varied thicknesses. This piece is caused to float on the surface of molten solder at a specified temperature with the metallic film facing the side of the solder, and the time required for this metallic film to become completely dissolved is measured from the backside of the glass surface. A graph showing the correlation between the metal concentration and the dissolution time is assumed to have been preliminarily prepared so that the metal concentration in the solder can be determined from such a graph.

By this method, it is important to be able to optically determine the end of a dissolution process accurately. For this reason, the color of this metallic film must be different from that of the molten solder. If it is copper or only the tin-lead composition that is to be detected, for example, the choice should be copper//glass because the color which is characteristic of metallic copper changes to a color of molten solder with metallic luster. If it is nickel, zinc, silver, cadmium, antimony or bismuth that is to be detected, the layer structure might be M//gold-1000A//chromium-50A//glass where M indicates one of these metals. This choice is made both because gold has a characteristic color and also because its rate of dissolution is extremely high so that the time required for its dissolution can be ignored compared to the time required for dissolving M. As in the case of copper, the end of the dissolution process of M is determined by observing the time when the characteristic color of gold changes to that of molten solder. The purpose of the chromium layer inbetween is merely to ensure a firm contact of gold with the glass substrate.

This method, making it possible to speedily detect metal concentrations in molten solder, should be considered very useful especially for preventing electrocorrosion of electric circuit boards by silver and abnormal rate of oxidation which may be caused if impurities got mixed in at the time of soldering. There are, however, a number of practical difficulties associated with this method.

Firstly, the surface of molten solder is usually covered by coarse solidified layers because the solder surface is always in contact with the atmosphere and there are many layers of metal oxides with small specific weights. Even if the surface is washed before the detector is placed, these layers appear instantly. In other words, it is inevitable that some oxides and solidified substances are found at the boundary between the metal film and the solder surface. This is particularly true with zinc as a component of brass which is frequently used for soldering.

Secondly, a layer of oil commonly called "topping oil" is frequently used industrially. Such an oil layer makes the optical measurement difficult. Thirdly, it is difficult to accurately control the surface temperature of molten solder at a constant level. This can affect the accuracy of measurement significantly. Fourthly, the solder and sample surfaces are not completely in thermal equilibrium when the sample is initially caused to float in the molten solder and time measurement is started. Moreover, one cannot ignore the time taken for the surfaces to come in contact through a flux layer. Of the four types of difficulties mentioned above, the first three are caused because the measurement must take place at the solder surface and the last one is due to the structure of the detector.

It is therefore an object of the present invention to provide an improved detector of impurities in molten solder which is practical to use and capable of yielding accurate results.

It is another object of the present invention to provide an improved optical measurement system for a detector of impurities in molten solder which is adapted to measure the rate of dissolution of a metallic film to determine the types and concentrations of impurities as well as the tin-lead composition of the solder.

It is a further object of the present invention to provide an optical transmission system for a detector of impurities in molten solder of the type described above so that optical measurements need not be performed in a hostile environment.

These and other objects are attained, as will be described below in detail, by providing a detector in the form of a light-transmissive rod with the cross-sectional area at one end covered by a metallic film. This covered end is adapted to be placed inside molten solder and the time required for the complete dissolution of the film is measured optically from the other end. A number of embodiments will be disclosed below including the use of a non-soluble metallic layer on the side surface of the rod in order to reduce optical noise, but the descriptions to be given below are not intended to limit the scope of the invention.

FIG. 1 is a graph showing the relationship between dissolution time and film thickness.

FIG. 2 is a diagonal view schematically showing one end of a light-transmissive rod for an impurity detector according to an embodiment of the present invention.

FIG. 3 is a cross-sectional side view which shows the structure of a metallic film with a gold layer.

FIG. 4 is a cross-sectional side view showing the structure at an end portion of a rod according to another embodiment of the present invention.

FIG. 5 is a schematic showing the structure of a rod according to still another embodiment of the present invention adapted to take in external light through a portion, of its side surface.

FIG. 6 is a schematic showing the structure of an entire detector system of the present invention according to a still further embodiment using an optical fiber to connect a light-transmissive rod with an optical measurement system.

FIG. 7 is a sketch schematically showing a light guide section of an optical fiber cable.

FIG. 8 is a sketch of a cross-sectional view of a junction between a light guide section of an optical fiber cable and a light-transmissive rod of the present invention when their diameters exactly match.

FIGS. 9(a) and 9(b) show schematically the use of a lens and a self-focusing fiber, respectively, at the junction between an optical fiber cable and a light-transmissive rod of the present invention.

FIG. 10 is a simplified diagram showing a basic junction structure for bending a light path.

A detector of impurities according to the present invention is characterized in that a light-transmissive rod is used where a thin glass plate was used by the conventional method described above. This light-transmissive rod may be made of silicate glass, or it may have silicate glass as principal constituent mixed with one or more of other types such as borosilicate glass, alkali silicate glass, soda lime glass, potassium lime glass, lead glass and barium glass.

The cross-sectional area at one end of this rod is covered by a metallic film which is adapted to be put inside the molten solder to be tested. Optical measurement is adapted to be conducted from the other end of the rod which is protruding outside the liquid.

The aforementioned metallic film may be a copper film of thickness in the range of 1000A to 30 $\mu$m. If necessary, it may be a layer of one o the following metals: zinc, nickel, silver, cadmium, antimony and bismuth. It should have a similar thickness and may include a gold layer as substrate. Such metallic film may be formed by a non-electrolytic plating method, a vacuum deposition method, a sputtering method, a chemical transport method or a combination of any two of the above. Alternatively, one of the methods mentioned above may be combined with an electrolytic plating method.

The aforementioned light-transmissive rod must satisfy a number of conditions. Not only should its transmissivity be sufficiently large for the visible light used for the measurement, but it should be able to withstand a temperature of about 320° C. without becoming deformed because one of its ends is adapted to be placed inside molten solder. It should not form an alloy with tin or lead at such temperatures and its thermal conductivity should be sufficiently small so that thermal equilibrium can be established quickly at the contact surface between the molten solder and the metallic film. Moreover, its coefficient of thermal expansion should be small so that the metallic film can stay on the rod and it must have sufficient mechanical strength so as to withstand the general handling of the detector. In addition, it must be chemically stable as a substrate. As long as these conditions can be satisfied, therefore, the light-transmissive rod may be made of materials other than glass such as single-crystalline materials like quartz and corundum, PLZT and heat-resistant polymer materials.

As for the shape, the rod need not be a circular cylinder. It may have an elliptical or polygonal cross-sectional shape. It may even be conical as long as optical measurements are allowed. Experimentally, however, a diameter in the range of 1mm to 10 mm and a length in the range of 50mm to 1000 mm seem preferable from the points of view of both manufacturing and measurement.

A major cause of error in measurement by the prior art technologies was that measurement had to be started as soon as a detector is placed on the solder surface so that dissolution takes place partially under conditions of thermal inequilibrium. According to the method of the present invention, three rods with metallic films of thickness respectively 1 $\mu$m, 4 $\mu$m and 7 $\mu$m, for example, are placed in molten solder simultaneously and measurement of time is started when the end of the dissolution process is detected from the first rod. At this moment, the film thicknesses of the remaining two rods are naturally 3 $\mu$m and 6 $\mu$m, respectively. At a still later time when the completion of dissolution is detected from the second rod, the film thickness of the third rod is 3 $\mu$m. The time for completing dissolution is also measured for the third rod. In other words, time is measured for the dissolution of 3 $\mu$m and 6 $\mu$m segments. If thermal equilibrium is not established immediately at the beginning, the curve representing the relationship between dissolution time and film thickness does not pass through the origin as shown in FIG. 1. It is clear that the method described above eliminates this problem. A few of actual test experiments which have been performed will be described next.

In Experiment 1, use is made of a silicate glass rod of diameter 5 mm and length 100 mm having a flat cross-section which has been sufficiently polished. A pretreatment process for non-electrolytic plating is carried out on the cross-sectional surface at one end with a $SnCl_2.HCl$ solution as sensitizer and a $PdCl_2.HCl$ solution as activator. It is then suspended in a separately prepared non-electrolytic copper plating liquid until a predetermined thickness is obtained. After it is pulled out of the liquid, it is washed with water and pure water and then quickly placed in acetone and trichlorethylene successively in this order for drying. Immediately thereafter, a preflux is applied on the copper film as a protective layer. An experimentally obtained correlation curve between the thickness of deposited film and time is utilized for the non-electrolytic plating.

The rate of deposition in this experiment was 1 $\mu m/600$ sec. Films with thicknesses '$\mu$m, 4 $\mu$m and 7 $\mu$m were produced. since the rate of deposition must be controlled in order to obtain a film of fixed thickness with a high level of accuracy, it is preferable to use a large amount of plating liquid and to keep the copper concentration not so high. It is also important to maintain the temperature accurately and to let the generated hydrogen gas escape carefully.

The film thus generated is deposited not only on the intended cross-sectional area 3 at one end of a rod 1 but frequently also on the side surface 2 as shown in FIG. 2. Although this is by no means a favored phenomenon, it hardly affects the accuracy of measurement by the detector.

In Experiment 2, to which FIG. 3 relates, use is made of a silicate glass rod 4 having a polished flat cross-sectional area of diameter 5 mm and length 10 mm. One of its ends is used as a substrate and a chromium layer 5 of 50Å to 300Å in thickness is formed first by a vacuum vapor deposition method. A gold layer 6 of thickness about 1000Å is subsequently formed on this chromium layer 5. These thicknesses, however, have no direct effect on the accuracy of measurement by this detector but the gold layer must be thick enough to exhibit the characteristic color of gold. Thereafter, it is suspended in a separately prepared non-electrolytic nickel plating liquid. Three nickel films 7 with thicknesses 1 $\mu$m, 3 $\mu$m and 5 $\mu$m were obtained at the deposition rate of 1 $\mu m/300$ sec. The remaining processes were the same as in Experiment 1.

The procedures for obtaining a film with accurate thickness are essentially the same as explained above regarding Experiment 1. In the case of the non-electrolytic plating liquid of this experiment, however, the solder temperature must be kept slightly higher and this unavoidably increases the deposition rate. It is also unavoidable because of the composition of the electrolyte that the film contains about 7 wt% of phosphorus.

Non-electrolytic plating of silver and zinc on a gold layer can be effected basically in the same way. In cases of cadmium, antimony and bismuth, however, the film should be grown to the desired thickness within the same apparatus used for the vapor deposition of gold layer. Preflux is applied immediately as a protective film after the rod is taken out of the apparatus.

The samples obtained in Experiments 1 and 2 were tested for individual metal types in sets of three with different thicknesses. The end of a light-transmissive rod with a metallic film is put inside a liquid flux for about ten seconds with stirring. The aforementioned preflux layer is thereby dissolved and at the same time flux is applied on the metallic surface. Thereafter, it is placed near the surface of molten solder and pre-heated for about 30 seconds. This is to let the flux dissolve the metal oxides formed on the film surface and further to activate the surface. A detector composed of three rods is then placed inside molten solder at an optional depth and the dissolution time is measured as described before.

In the case of molten tin-lead solder (60Sn/40Pb) free of impurities at 260±1° C., for example, the dissolution times of copper films of thickness 4 $\mu$m and 7 $\mu$m were respectively 71 seconds and 142 seconds from the time when the sample with thickness 1 $\mu$m was completely dissolved. The time required to dissolve the film of thickness 1 $\mu$m was about 27 seconds. With a solder sample containing 0.5 wt% of copper, on the other hand, the corresponding dissolution times were 130 and 258 seconds and the time for dissolving a copper film of thickness 1 $\mu$m was about 45 seconds after it was put inside the molten solder.

As for nickel films of thickness 1 $\mu$m, the dissolution time was about 25 seconds in molten solder free of impurities and about 60 seconds in molten solder containing about 0.1 wt% of nickel which is said to be the saturation point of dissolution regarding the solder.

As for the change in composition, the dissolution time of copper film increases by about 6% for each reduction by 1wt% in the concentration of tin from the original value of 60 wt% at 260° C. This shows that changes in composition as well as metal impurities at low concentrations can be sensitively detected by this method.

The impurity detector of this invention can be improved further from the embodiments described above. In one aspect, since the length of the portion of light-transmissive rod to be immersed in the solder or to be exposed to external light is not strictly fixed, the rod may appear to have extra boundary surfaces associated with it, each affecting the absorption and reflection of visible and ultraviolet beams used as incident light. This causes variations in the optical response and affects the accuracy of optical detection.

Unwanted effects of external light can be eliminated or standardized in principle if the detector is always so set that the length of the portion of the rod to be immersed or to be exposed is the same. In practice, however, it is not easy to regulate such distances strictly. When the molten solder is stirred and the solder surface moves up and down during a measurement, this method is not practical at all. In addition, flux and oxide layers floating on the solder surface tend to splash and get attached on the side surface of the rod. In order to eliminate difficulties of this type, the peripheral or side surface of the light-transmissive rod of the present invention may preferably be covered by a light-screening metallic or carbon layer which is insoluble in the molten solder.

With the commonly used 60Sn/40Pb solder, soldering temperature is usually in the range between 260° C. and 320° C. but no organic polymer film with light-screening property which is stable in this temperature range has yet been discovered. On the other hand, metals like titanium, vanadium, chromium, manganese, molybdenum and tungsten are considered not to dissolve easily at these temperatures. Since the experiments carried out by the present inventor show that about 0.01 wt% of aluminum dissolves in 60Sn/40Pb solder at 500° C. in 13 hours, nearly 0 wt% of iron under the same conditions and about 0.1 wt% of arsenic under the same conditions in five hours, it may be concluded that these metals as well as alloys having at least one of these metals as constituent can be used for the aforementioned purpose. Even nickel, with small dissolution rate and saturation concentration of about 0.1 wt% at 260° C., may be considered a usable metal. Since all these metals, with the exception of nickel, are difficult to use for direct plating on a non-conductive rod, a nickel or copper layer must be formed first as a substrate by a non-electrolytic plating method. Respective metallic layers can be formed thereon by an electrolytic plating method. Such procedures are the most economical and effective.

Besides metals, carbon may be used for the light-screening purpose. A uniform carbon layer can be obtained by applying a dispersive coating material known by the name of colloidal carbon uniformly over the rod and sintering it at a relatively low temperature. Since the thickness of this layer need not be controlled particularly, such materials may be used.

Among metallic foils, aluminum foils are the most common examples. They can be used by tightly covering the rod so as not to leave any space on the surface of the rod but there are difficulties relating to obtaining uniform boundary surfaces and the problem of fluctuations among the rods. Seriousness of these problems is all relative to the sensitivity of the system for optical measurement.

FIG. 4 is a cross-sectional view of a light-transmissive rod at one end according to another embodiment of the present invention. In this figure, numerals 11, 12 and 13 respectively indicate a quartz rod, a nickel substrate and a chromium layer. Numeral 14 indicates a film of the same metal as that to be detected. Numeral 15 indicates a polished cross-sectional surface of the quartz rod 11. A method of fabricating such a rod will be described next.

A 99% quartz rod of diameter 1 mm and length 220 mm is lightly etched with a mixed $6HNO_3$-FH solution and is then subjected to a pretreatment with a $SnCl_2$-HCl solution as sensitizer and a $PbCl_2$-HCl solution as activator. Thereafter, the nickel layer 12 of any thickness between 0.5 and 1 $\mu$m is formed on the peripheral part of the rod 11 as shown in FIG. 4 by a non-electrolytic plating method. Next, a chromium surface layer 13 of thickness about 0.7 $\mu$m is formed by an electrolytic plating method. Thereafter, both ends of the rod 11 are cut by a cutter equipped with a carbon blade or a diamond blade. The cross-sectional areas are polished and a rod of total length 200 mm is prepared. A layer 14 of the same type of metal as that to be detected is formed accurately with proper thickness on one of the end cross-sectional areas and optical measurement is carried out from the other end cross-sectional area. If a non-electrolytic plating method is used for the formation of the metallic layer 14, the layer frequently extends over to the peripheral surface as shown in FIG. 2.

According to the embodiment described immediately above, the peripheral, or side surface of the rod is entirely covered by the light-screen layer. Depending on the type of optical measurement system to be used with this detector, however, it may be necessary to take in external light to a certain extent. In such a situation, a coating material with teflon particles may be applied to a certain portion of the side surface before the aforementioned pretreatment for non-electrolytic plating is carried out on the quartz rod 11. This material is dissolved again in an organic solvent after the pretreatment is completed. By this method, deposition of metallic palladium can be selectively prevented and the subsequent non-electrolytic and electrolytic plating steps are made ineffective. FIG. 5 is a schematic which shows the structure of a light-transmissive rod of the present invention adapted to take in external light through a portion of its side surface. In FIG. 5, numeral 16 indicates an optical measurement system, numeral 17 indicates an uncovered portion, numeral 18 indicates a covered portion, numeral 19 indicates the surface of molten solder and numeral 20 indicates a film of the same type of metal as that to be detected.

The uncovered portion 17 may be selected freely, depending on the type and sensitivity of the light measuring system 16, as long as the original purpose of providing a light-screening layer, or the covered portion 18, remains satisfied. When a plurality of rods having metallic films of different thicknesses are used simultaneously as explained above, for example, in a situation where three rods with films of thicknesses 1 $\mu$m, 4 $\mu$m and 7 $\mu$m are immersed simultaneously in molten solder and time measurements are started when the 1 $\mu$m-film has been completely dissolved, however, the uncovered portions of the rods must naturally be made uniform in order to eliminate fluctuations among the rods regarding incident light from outside, or optical zero-point adjustment must be carried out individually for all rods.

Many advantages are gained by this embodiment of the present invention. Because of the light-screening layer on the side surface, it is not necessary any more to control the external light conditions during measurements or to adjust the immersed or exposed length of the rod. Moreover, effects due to vertical motion of the solder surface during measurements may be ignored and measurements are not affected by the contaminants getting attached on the side surface of the rod. From the point of view of optical measurement, use of light-screening layer has made it possible to use very weak incident light and also to obtain wavelength effects peculiar to the incident light. In addition, improved response sensitivity can be obtained by this embodiment of the present invention.

In spite of the many advantages which are made available by the present invention, it is still inconvenient if the optical measurement system schematically shown in FIG. 5 is directly connected with the detector of the present invention to form a unitized structure so that its operation and measurements must take place directly above the molten solder. Firstly, the atmosphere directly above the molten solder is filled with the vapor of preflux and flux which gets easily attached to any surface. It is not an appropriate place to position an optical means. Secondly, the solder temperature is usually in the range of 260° C. to 320° C. and the optical measuring system positioned only 8 cm to 10 cm above the solder surface would become overheated. Thirdly, the space immediately above the solder surface is generally not a convenient place to put any measurement means. There are many lines to be passed in this space and it is inconvenient also from the point of view of operability.

For these reasons, there is still another embodiment of the present invention, the object of which is to separate the aforementioned light-transmissive rod from both the light source and the optical measurement system so that the latter can be placed farther away from the molten solder where there will be no problem of operability. According to this embodiment of the invention, this and other objects are attained by using an optical fiber to connect the optical measurement system with the upper end surface of the rod and using it as a passage way both for the incident beam from a light source and the reflected beam from the film surface at the immersed end of the rod.

FIG. 6 is a schematic showing the structure of an entire detector system of the present invention according to the aforementioned embodiment using an optical fiber to connect a detector rod with an optical measurement system. In FIG. 6, numerals 21 and 22 respectively indicate a light source and an optical measurement system. Numerals 23 and 24 respectively indicate an incident light optical fiber cable and a reflected light optical fiber cable. Numeral 25 is a joined optical fiber cable. Numeral 26 indicates a connecting surface inside a connector. Numerals 27 and 28 indicate respectively a light-transmissive rod and molten solder. Although only one rod 27 is shown for simplicity, a real system includes three such rods having metallic films of different thicknesses as described before in connection with another embodiment. An optical fiber cable of length 1.2 m is connected to each of these rods and the times required to completely dissolve the metal films are successively measured. The same light source is used for all rods and the reflected beams are analyzed together in parallel by the same measurement system. As for the wavelength of the source, the source is so designed that an optional wavelength zone where highest sensitivity can be obtained regarding the metallic films and the molten solder can be selected freely within the range of 300 nm to 1000 nm. The light-transmissive rod 27 is made of quartz and is 5 mm in diameter and 100 mm in length. Both its end covered by a metallic film and the other end connected to an optical fiber are polished with SiC particles. The structure of the rod 27 is the same as shown in and explained in connection with FIG. 4 except regarding diameter and length.

Described summarily, FIG. 6 shows that the light-transmissive rod 27 according to this embodiment is covered at one end by a metallic film and connected at the other to an optical fiber cable 25 which is flexible and of optional length. A total length 2 m is sufficient and the cable is not specifically required to have a low transmission loss. As long as the intended functions of this system can be carried out, there are no particular limitations regarding its material, index of refraction, fiber diameter, cover material or cable diameter. It is desirable, however, that the core material has its transmissive wavelength zone between the near infrared (about 1000 nm) and the near ultraviolet (about 300 nm). As for transmission loss, requirements are not as severe as those for optical communication fibers but it is generally considered the better, the more transparent it is. As for the cover material, it naturally goes without saying that its index of refraction must be smaller than that of the core material and that its coefficient of thermal expansion should be either about the same or at least such that the internal stress will not exceed the critical value of the structural materials.

From the structural requirement, the optical fiber for the incident light and that for the reflected light must be joined together into one fiber cable connected to the rod. Moreover, these fibers must be so arranged at the connecting surface that optical paths are established for the measurement of absorption and reflection.

Since the light-transmissive rod of this invention is intended to be used only once for each measurement, it must be removable from the optical fiber after each measurement so that another one can be attached for the next measurement. Accordingly, the aforementioned two sections should not be fused together. They should be joined removably from each other.

In order to make absorption-reflection measurements possible, the sections may either be in tight contact with each other across a junction plain or, if necessary, be separated from each other by a predetermined distance. In the latter situation, an oil with index of refraction similar to that of the fiber may be used to wet the ends so as to reduce the transmission loss at the junction plain. If the light-guide part of the fiber cable cannot match the diameter of the light-transmissive rod, or if it is desired for a different reason to converge or diverge the light beam, a lens or a self-focusing fiber may be used. Additionally, a fiber plate may be inserted at the junction plain, if necessary, and prisms and mirrors may also be used whenever the angle of optical path must be changed.

Referring again to FIG. 6, the quartz rod 27 is disconnected from the connector 26 after the metallic film at its lower end has been completely dissolved. After a chemical etching is performed, and after another metallic film of a desired thickness is formed, the rod is ready to be used again for another measurement.

The optical fiber is made of quartz core materials of diameter several 10 μm and a silicone resin coating as cover material. FIG. 7 shows a light guide section 29 of a fiber cable with a diameter of 1.3 nm. Large numbers of incident light fibers 31 and reflective light fibers 32 are densely bound together with a coating material 30. FIG. 8 is a simplified sketch showing the junction between the light guide section 29 and the light-transmissive rod 27 in an ideal situation where their diameters exactly match.

In most cases, however, matching by using a lens 33 as shown in FIG. 9(a) or a self-focusing fiber 34 as shown in FIG. 9(b) is basically more appropriate and economical. Explained more in detail, a metallic film having a satisfactorily uniform thickness cannot be obtained on the end cross-sectional surface of a rod by an electrolytic or non-electrolytic plating method if the diameter is several mm. According to the present invention, the minimum rod diameter is 5 mm. On the other hand, the light guide sections of fiberscopes currently being used in medical and industrial fields have diameters in the range of 9 mm to about 20 mm, while the diameter of the most commonly used fiber cable is only several mm. In view of the costs of optical fiber cables with a light guide of diameter 5 mm or greater, the connecting methods shown in FIGS. 9(a) and 9(b) seem more advantageous. The above, however, is not a definite conclusion, especially if a vacuum vapor deposition method, a sputtering method or a chemical transport method is used in the production of metallic film so that a film with a uniform thickness distribution can be obtained over a very small cross-sectional area.

FIG. 10 shows a basic junction structure for bending a light path including a prism 35. The prism 35 may be substituted by a mirror. In short, the basic optical system of an image guide used in a fiberscope can be directly used in the connector section. When the concentration of a metal dissolved in molten solder is nearly at a saturation level, it frequently happens according to the present inventor's experience that dissolution of the metallic film covering the bottom end of a rod becomes extremely slow and that the dissolution does not always proceed uniformly near the end so that island-like patches are left especially near the center of the cross-sectional area of the rod. In such a situation, it is not easy to accurately determine the end time of dissolution simply be observing the reflected light and it becomes necessary to observe the end cross-sectional area as an image. For this purpose, more accurate transmission mechanism such as the use of a fiber plate may be considered.

In summary, impurity detectors according to this embodiment are easy to use because of the freedom in choosing where to install the optical measurement system. Since the optical measurement system can be freed from the effects of heat and vapors immediately above molten solder, its maintenance is simplified and operability is improved. In particular, effects of heat need no longer be considered in designing a circuit for the optical measurement system and accessories. From the point of view of accuracy, drifts due to heat are diminished. Since the light source and the optical measurement system need not be moved with the rod when the latter is put inside a solder sample, errors in reading drop significantly.

What is claimed is:

1. A detector of impurities in molten solder for detecting kinds and concentrations of impurity metals in molten solder or changes in the tin-lead composition thereof by measuring the dissolution rate of a film of the same metal as that to be detected or a copper film, said detector comprising
    a light-transmissive rod having a first end cross-sectional area and a second end cross-sectional area at opposite ends thereof,
    a metallic film coveringly attached to said first end cross-sectional area of said rod,
    measuring means for optically measuring the dissolution time of said metallic film through said second end cross-sectional area while said first end cross-sectional area is immersed in molten solder,
    a light-screening layer coveringly attached to the peripheral or side section of said rod, said light-screen layer being insoluble in molten solder.

2. The detector of claim 1 wherein said light-screening layer is a metal or colloidal carbon.

3. The detector of claim 1 wherein said light-screening layer is a metallic layer or a metallic foil of a metal selected from a group consisting of aluminum, titanium, vanadium, chromium, manganese, iron, nickel, arsenic, molybdenum and tungsten, or an alloy containing a metal selected from said group.

4. A detector of impurities in molten solder for detector kinds and concentrations of impurity metals in molten solder or changes in the tin-lead composition thereof by measuring the dissolution rate of a film of the same metal as that to be detected or a copper film, said detector comprising
    a light-transmissive rod having a first end cross-sectional area and a second end cross-sectional area at opposite ends thereof,
    a metallic film coveringly attached to said first end cross-sectional area of said rod, the dissolution time of said metallic film being optically measurable through said second end cross-sectional area when said first end cross-sectional area is immersed in molten solder, and
    a light-screening layer coveringly attached to the peripheral or side section of said rod, said light-screening layer being insoluble in molten solder.

* * * * *